United States Patent [19]

Dayton

[11] Patent Number: 5,578,075
[45] Date of Patent: Nov. 26, 1996

[54] MINIMALLY INVASIVE BIOACTIVATED ENDOPROSTHESIS FOR VESSEL REPAIR

[75] Inventor: Michael P. Dayton, 14802 Hadleigh Way, Tampa, Fla. 33624

[73] Assignees: Michael Peck Dayton, Tampa, Fla.; Kenneth Granke, Morgantown, W. Va.

[21] Appl. No.: 457,850

[22] Filed: Jun. 1, 1995

Related U.S. Application Data

[63] Continuation-in-part of Ser. No. 204,947, Mar. 2, 1994, Pat. No. 5,449,382, which is a continuation of Ser. No. 971,217, Nov. 4, 1992, abandoned.

[51] Int. Cl.$^6$ .......................................... A61F 2/06
[52] U.S. Cl. ........................ 623/1; 623/12; 623/901; 604/104; 604/107
[58] Field of Search .................... 623/1, 12, 901; 604/95, 104, 107, 114

[56] References Cited

U.S. PATENT DOCUMENTS

| | | | |
|---|---|---|---|
| 4,740,207 | 4/1988 | Kreamer | 623/12 |
| 5,019,090 | 5/1991 | Pinchuk | 623/1 |
| 5,123,917 | 6/1992 | Lee | 623/1 |
| 5,234,456 | 8/1993 | Silvestrini | 623/1 |
| 5,342,348 | 8/1994 | Kaplan | 623/13 |
| 5,344,426 | 9/1994 | Lau et al. | 623/1 |
| 5,449,382 | 9/1995 | Dayton | 623/12 |
| 5,464,450 | 11/1995 | Buscemi et al. | 623/12 |

*Primary Examiner*—Paul B. Prebilic
*Attorney, Agent, or Firm*—John S. Munday; Stephen G. Stanton

[57] ABSTRACT

A minimally invasive bioactivated endoprosthesis device for vessel repair. The device comprises a stent which is formed from metal or polymers into a predetermined shape which may include a plurality of holes patterned with a desired size, shape and number. The stent is then coated with a polymer or is formed from a polymer which contains a bioactive substance which achieves an equilibrium with the surrounding body tissues or fluids, with the equilibrium being controlled by charge distribution, concentration and molecular weight of the bioactive substance in relation to the pore size of the polymeric carrier for controlled prolonged release of said bioactive substance. The bioactive substance may be selected from the group of heparin, hirudin, prostacyclenes and analogs thereof, antithrombogenic agents, steroids, ibuprofen, antimicrobials, antibiotics, tissue plasma activators, rifamicin, monoclonal antibodies, snake venom protein by-products, antifibrosis agents, hyaluronte, cyclosporine and mixtures of these bioactive substances for simultaneous multiple treatments. The stent itself may take several distinct configurations. Preferred is a stent which comprises a substructure selected from flat sheets, flat sheets having holes therein, meshes and stent frames having a sheath thereon, and the substructure is coated with a polymer embedded with a bioactive substance. The stent may be either self-expandable or mechanically expandable, such as by a balloon or other device.

11 Claims, 3 Drawing Sheets

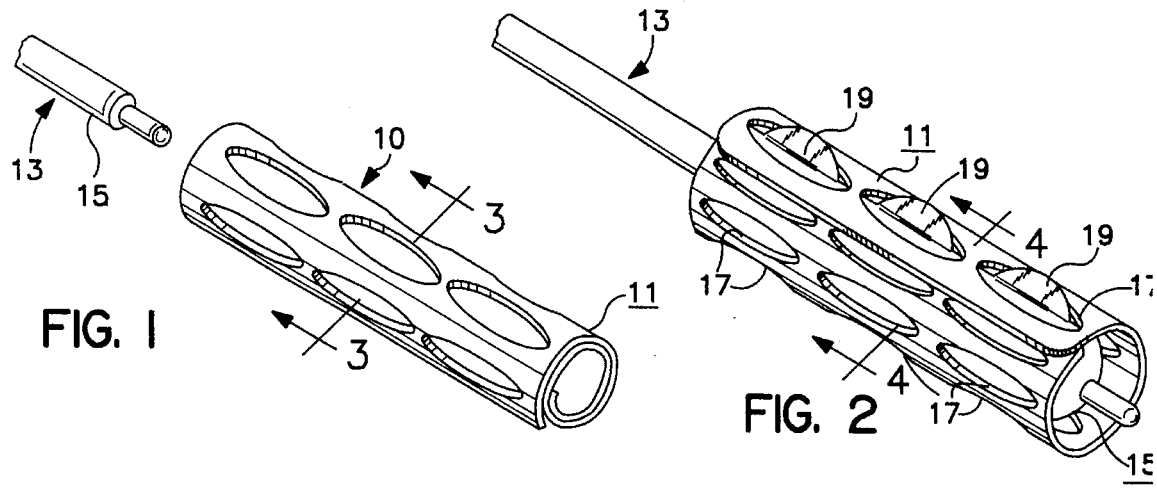
FIG. 1
FIG. 2
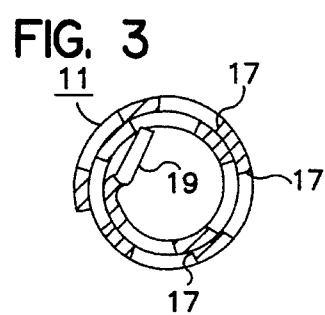
FIG. 3
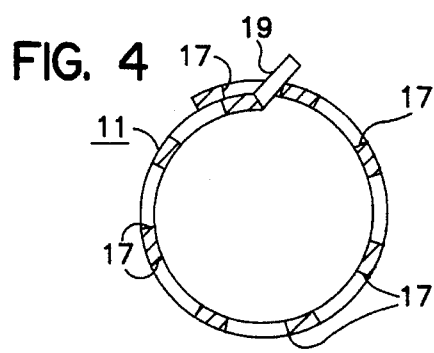
FIG. 4
FIG. 6
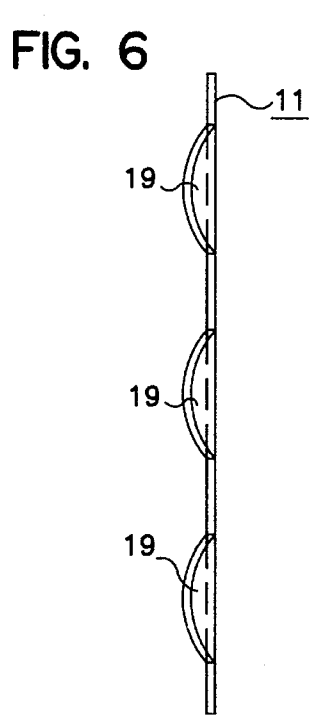
FIG. 5
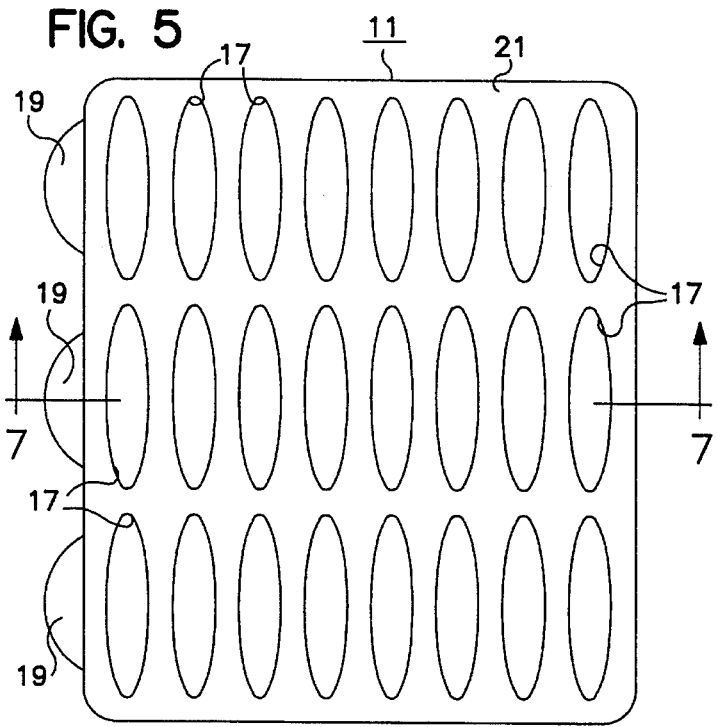
FIG. 7
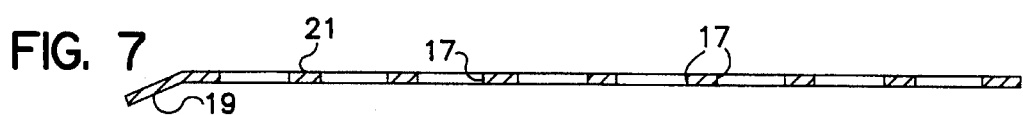

MINIMALLY INVASIVE BIOACTIVATED ENDOPROSTHESIS FOR VESSEL REPAIR

This is a continuation-in-part of my prior application filed Mar. 2, 1994, having Ser. No. 08/204,947, now U.S. Pat. No. 5,449,382, which in turn is a continuation of my prior application filed Nov. 4, 1992, having Ser. No. 07/971,217, now abandoned.

FIELD OF THE INVENTION

The present invention relates to an improved percutaneously inserted endoprosthesis device which is permanently or temporarily implanted within a body vessel, typically a blood vessel. More particularly, the present invention relates to a new procedure for administering localized bioactive substances via prostheses designs which are adapted to resist problems associated with restenosis, thrombosis, infection calcification and/or fibrosis after implantation.

BACKGROUND OF THE INVENTION

In certain medical treatment procedures, a type of endoprosthesis device known as a stent is placed or implanted within a blood vessel for treating various problems such as stenonses, strictures, or aneurysms in the blood vessel. These devices are implanted within the vascular system to reinforce collapsing, partially occluded, weakened or abnormally dilated sections of the blood vessel. Stents may also be implanted in the ureter, urethra, bile duct, or any body vessel which has been narrowed, weakened or in any of the other ways which requires reinforcement.

A common approach for implanting stents in peripheral or coronary arteries is to first open the constricted region of the vessel via a percutaneous transluminally inserted angioplasty balloon catheter. The uninflated balloon at the tip of the catheter is advanced into the narrowed portion of the vessel lumen. The balloon is inflated so as to push the stenotic plaque outward, thereby enlarging the luminal diameter. Thereafter another catheter containing the stent is advanced to the region just enlarged by the balloon catheter and the stent is deployed. The catheter is withdrawn leaving the stent within the vessel.

The concept of implanting transluminally placed coil spring stents within an artery is not new. In one experiment in 1969, six stents were implanted in arteries of dogs. Three stents were stainless steel covered with silicone rubber and the other three stents were bare stainless steel. All three silicone coated stents occluded within 24 hours while two of the three bare stents remained open for thirty months. The stents were deployed using a pusher catheter having the same outer diameter as the stent.

In 1983, thermally expandable stents were reported, in which an alloy wire was shaped at thigh temperature into a stent configuration. Later it was straightened at room temperature into a configuration suitable for transluminal placement. Once placed within the vessel the stent was exposed to elevated temperatures to cause the alloy to return to its initial coil configuration. Canine studies of these stents, using the alloy nitinol, an alloy of nickel and titanium, demonstrated restenosis and intimal thickening 8 weeks following implant.

In 1984, self-expanding stents were described in which a device was introduced percutaneously after torsion reduction and was deployed by applying a reverse torsion in-vivo. This type of device proved to be complex and limited by a small expansion ration. Another self-expanding stent used stainless steel wire in a zig zag configuration which resulted in incomplete vascular contact and only partial healing of the device. Yet another mechanical self-expanding stent was reported where a woven multifiliment stainless steel stent was deployed by a catheter with a constricting outer sleeve. Once in place, the outer sleeve was removed allowing self-expansion of the spring stent against the vessel wall.

Thrombosis occurred in these early prototypes, especially when the vessel tapered, and at branch points and at low expansion ratios. Canine aortic implantation resulted in multiple areas of vessel-to-stent adhesion at 3 weeks following implant. The stent exhibited minimal thrombogenicity.

Balloon expandable stents were first reported as being constructed of woven stainless steel wire where the cross points were silver soldered to resist radial collapse. The stent was deployed unexpanded over a balloon catheter, and once in position the stent was expanded by the outward force of the balloon. 8 of 11 stents implanted remained open for 1 to 8 weeks. It has been observed that the amount of intimal hyperplasia to be inversely proportional to the initial vessel lumen diameter. In another version, silver soldering cross points were replaced by the use of a stainless steel tube with rows of offset slots which became diamond shaped spaces. Although neointimal hyperplasia was observed, all stents remained open in rabbit aortas for 6 months.

Placement of a stent in a blood vessel is described in Lindemann et al U.S. Pat. No. 4,878,906 where a combination of sheath covered sleeve and a balloon catheter are used to locate and place the prosthesis. No recognition is given to the problems just discussed herein.

A prosthesis system using an expandable insert is shown in Garza et al U.S. Pat. No. 4,665,918, which is typical of those devices which are implanted without any express concern for the biocompatibility of the device being inserted. One can expect many of the foregoing problems and concerns to be evidenced by this device.

One device which is shown in U.S. Pat. No. 4,768,507 to Fischell et at describes a coil spring stent on which an application of a carbon coating or a carbon coated polytetrafluoroethylene has been applied on the surface of the coil spring. Fischell et al teaches that the thrombogenic potential of the device is reduced, through a passive methodology, but does nothing to address the biological response to the implant as a foreign body. Moreover, no suggestion is made of a way to inhibit neointimal hyperplasia, which inevitably follows balloon catheter induced injury to arterial vessels.

Yasuda U.S. Pat. No. 4,994,298 employs plasma polymerization to form a thin flexible coating on stents, teaching that improved biocompatibility, such as non-thrombogenicity and tissue or blood compatibility may be improved. Again this process is a passive methodology as previously described.

There are essentially two types of stents which have been employed in the prior art. Spring like stents have been inserted using a sheath or restraining element to keep the spring from expanding until It is in place. The other form of stent uses a method of expanding the stent once it is in place, such as a balloon catheter, Kreamer U.S. Pat. No. 4,740,207 describes one version of the balloon catheter version. In this patent, a semi-rigid tube which has a smaller relaxed diameter which is expanded to a larger operating diameter which Is maintained by a retaining ledge on the Inside of the graft. Concern here, of course, is that the inside located ledge and other retaining means may inadvertently function to cause further blockage of the tube once it is installed. Also, Kreamer states that the tube is held in place by friction between the outer periphery of the graft and the inner periphery of the vessel to prevent displacement of the grant once in place In the vessel. The obvious concern is that the size must be precise or the tube will expand too much or too little, either damaging the vessel or escaping from the location for which it was intended.

Prior art devices represent a foreign body that has no biologically active properties and thus are a factor which contributes in a major way to the eventual restenosis or thrombosis of the vessel. These prior art devices attempt to reduce neointimal hyperplasia passively by adjusting mechanical variables such as lowering the stent profile, coating the stent with carbon, or by making the stent more or less rigid or flexible.

Accordingly, it is an object of the present invention to provide a device and method for deploying stents in blood vessels and other regions of the body without concern for the precise size of the stent being employed or the size of the vessel being treated or repaired.

It is an important object of this invention to produce a stent device and delivery system for the stent which produces rapid endothelialization with the least mount of intimal hyperplasia. While this goal has been stated by others, no effective method or device has been proposed to accomplish that goal.

Another object of this invention is to provide an endoprosthesis device and method for its use in which problems associated with restenosis, thrombosis, infection calcification and/or fibrosis after implantation may be avoided.

Yet another object of the present invention is to provide a device which is effective in administering localized bioactive substances to prevent rejection and side effects from an implanted endoprosthesis device.

Other objects will appear hereinafter.

SUMMARY OF THE INVENTION

It has now been discovered that the above and other objects of the present invention may be accomplished in the following manner. Specifically, an minimally invasive bioactivated endoprosthesis for vessel repair has been discovered which is admirably suited for long term use in a variety of surgical procedures and treatments.

The device is intended for use in those medical treatment procedures where a type of endoprosthesis device known as a stent is placed or implanted within a blood vessel for treating various problems such as stenonses, strictures, or aneurysms in the blood vessel. These devices may also be implanted within the vascular system to reinforce collapsing, partially occluded, weakened or abnormally dilated sections of the blood vessel. Stents of the present invention may also be implanted in the ureter, urethra, bile duct, or any body vessel which has been narrowed, weakened or in any of the other ways which requires reinforcement.

The device comprises a minimally invasive bioactivated endoprosthesis device for vessel repair, including a stent which is formed from metal or polymers into a predetermined shape which includes a plurality of holes patterned with a desired size, shape and number to provide a desired bending modulus. The stent may be fabricated from stainless steel, nitinol or other appropriate metallic alloys or may be formed from a variety of polymers which are known to be suitable for use with the human body.

When a metallic stent is employed, it is formed and then coated with a polymer which contains a bioactive substance which achieves an equilibrium with the surrounding body tissues or fluids, with the equilibrium being controlled by charge distribution, concentration and molecular weight of the bioactive substance in relation to the pore size of the polymeric carrier. Among these polymers are polymers having a microporous structure, such as silicone, polyurethane, polyvinyl alcohol, polyethylene, biodegradable polylactic acid polymers, polyglycolic acid polymers, polyesters, hydrogels, tetrafluroethylene and polytetrafluroethylene, fluorosilicone, hyaluronte and combinations, copolymers and blended mixtures thereof.

If the stent is formed from a polymer, these same polymeric materials may be employed, although some may need to be structurally reinforced. Also useful as a polymeric stent is polymethylmethacrylate, which is an example of the generic class of structurally adequate polymers without reinforcement.

A bioactive substance is preferably admixed in the polymer for elution from the microporous structure of the stent or coating on the stent after implantation. The rate of elution of the bioactive substance is controlled by selecting a pore size for the microporous structure in response to the concentration and molecular weight of the bioactive substance to achieve equilibrium between the polymer and the tissue or fluids proximate the stent upon implant. This permits a controlled and prolonged release of the bioactive substance as the polymer eluded or when a bioresorbable polymer erodes to release the bioactive substance.

The bioactive substance may be selected from the group of heparin, hirudin, prostacyclenes and analogs thereof, antithrombogenic agents, steroids, ibuprofen, antimicrobials, antibiotics, tissue plasma activators, rifamicin, monoclonal antibodies, snake venom protein by-products, antifibrosis agents, cyclosporine, hyaluronte and mixtures of these bioactive substances for simultaneous multiple treatments.

The stent itself may take several distinct configurations, all of which have a predetermined biasing force acting on the diameter of the stent. A flat, rectangular strip of stent material is formed, with the size being determined by the size of the blood vessel or other body conduit where the stent will be placed. As previously set forth, the strip includes a plurality of holes patterned with a desired size, shape and number to provide a desired bending modulus. Locking tabs are provided to engage the some of the plurality of holes at the maximum expanded size to prevent return to the smaller diameter coiled shape.

Preferred is a rolled stent which is provided with a coiled shape to which it tends to return when expanded. This is accomplished by using the same edge of the strip on which the tabs are formed as a rotational axis to roll the strip into a tight coil so that the tabs are in the center of the coil. Heat is applied to cause the strip to take a set in this coiled shape, so that when the coiled strip is radially expanded or unrolled, the form stresses will bias the strip to roll back into the preferred shape. The tabs which have been formed on what is now the inside edge will engage the holes formed in the strip and prevent collapse to the biased shape. Since a plurality of holes are formed in the strip, the device may be expanded to different sizes, depending upon the particular vessel in which it is placed. Under some circumstances, the device is capable of assuming a stent shape with more than one diameter, for the first time in these applications.

Alternatively the predetermined bias of the stent may be the expanded size so that the stent is coiled against this bias during insertion. Holes are still placed in the sheet or strip to encourage adoption of the stent by the vessel. However, the relaxed or unbiased position is that of the intended final shape, and therefore locking tabs are not necessary. The stent is compressed or rolled to a smaller diameter prior to use with a built in bias to return to the "in use" shape previously built into the stent. This embodiment is installed using an introducer sheath. A balloon catheter may or may not be needed in view of the built in bias.

BRIEF DESCRIPTION OF THE DRAWINGS

For a more complete understanding of the invention, reference is hereby made to the drawings, in which:

FIG. 1 is an isometric view of an endoprosthesis for vessel repair.

FIG. 2 is an isometric view of the device shown in FIG. 1 in the most fully opened position.

FIG. 3 is a sectional view taken on line 3,3 of FIG. 1.

FIG. 4 is a sectional view taken on line 4,4 of FIG. 2.

FIG. 5 is a plan view development of the endoprosthesis blank prior to formation.

FIG. 6 is an end view of the device of FIG. 5 as viewed from the left hand side.

FIG. 7 is a sectional view taken on line 7,7 of FIG. 5.

DETAILED DESCRIPTION OF THE PREFERRED EMBODIMENT

Figure 8:
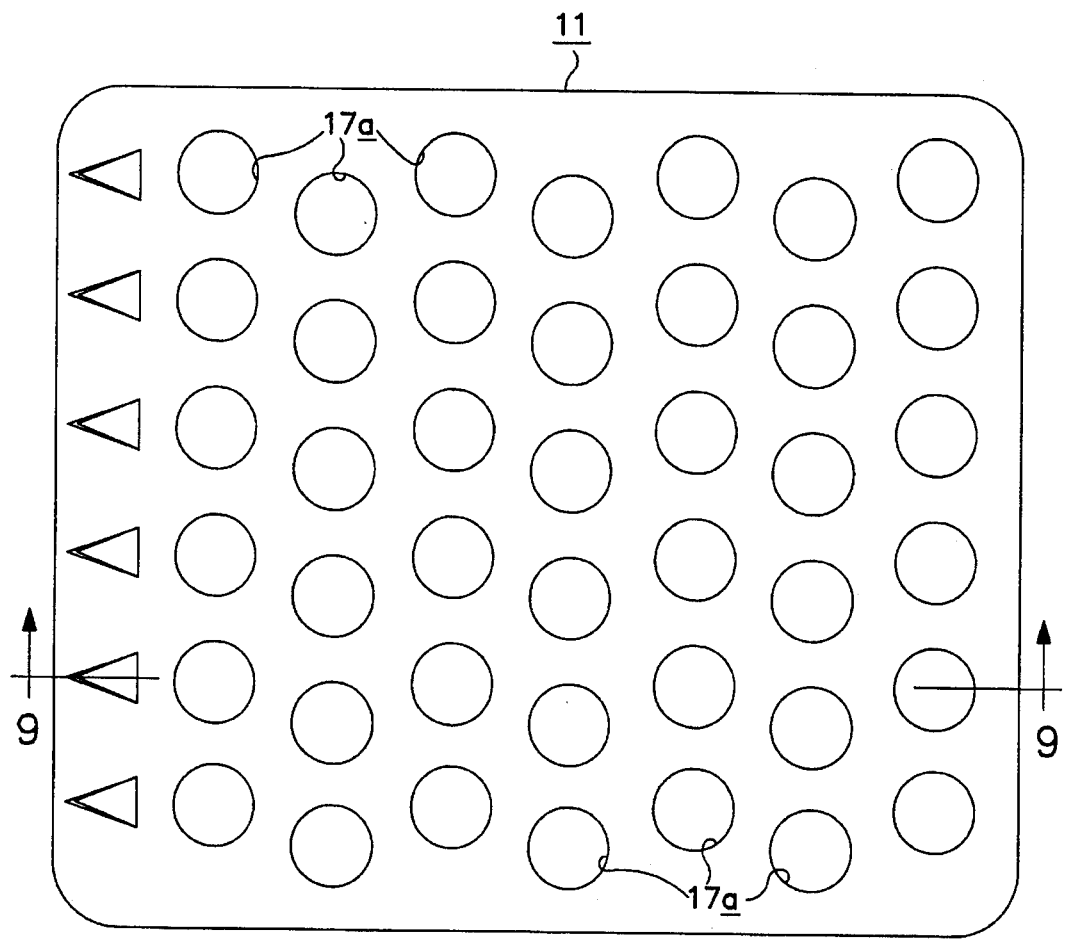
FIG. 8 is a plan view development of a second embodiment for an endoprosthesis blank.

As shown in the drawings, the device of this invention comprises a minimally invasive bioactivated endoprosthesis device, 10 generally, for vessel repair in contact with surrounding body tissues or fluids. The device includes a stent 11 which may be installed in the vessel using a catheter 13, and in some cases using a balloon 15 on the end of catheter 13. Stent 11, which contains a plurality of holes 17, is shown in a tightly coiled pre-insertion position in FIG. 1 with a fragment of balloon catheter 13 shown about to be inserted medially within the endoprosthesis. The sectional view shown in FIG. 3 illustrates a tab 19 which does not engage any holes 17 and which is enclosed within the coiled stent 11, as the stent is in its relaxed or steady state with no bias from external forces acting on the stent.

In FIG. 2, the stent 11 is illustrated in its most fully opened and locked position, as expansion has been effected diametrically by means of the medially positioned balloon 13. FIGS. 2 and 4 shows how the tab 19 engage holes 17 and prevent the stent from re-coiling upon itself to return to the position shown in FIG. 3.

The direction of the catheter and the balloon define an axis for reference to the various stents shown herein as part of the present invention. FIG. 5 is a plan view development prior to tightening and assembly of the stent into the predetermined shape. The stent 11 comprises a flat, rectangular strip 21 of a size determined by the size of the blood vessel or other body conduit where stent 11 will be placed. Tabs 19 extend along one end of strip 21 and are angled, as shown in FIG. 7. Strip 21 is coiled and biased to take a smaller diameter coiled shape, as tabs 19 engage some of the plurality of holes 17 at a maximum desired expanded size to prevent return to the smaller diameter coiled shape.

The coiled stent 11 is formed by using that edge of strip 21 on which the tabs 19 are formed as a rotational axis to roll the strip 21 into a tight coiled stent so that the tabs 19 are in the center so that when coiled strip 11 is radially unrolled to the position shown in FIG. 2, the form stresses will bias the strip 21 to roll back into the preferred shape of FIG. 3, and tabs 19 will engage holes 17 formed in strip 21, so as to prevent collapse to the biased shape of FIG. 3.

By using the same edge of the strip 21 on which the tabs 19 are formed as a rotational axis to roll the strip into a tight coil, tabs 19 are in the center of the coiled stent. Heat is applied to cause the strip to take a set in this coiled shape, so that when the coiled strip is radially expanded or unrolled, the form stresses will bias the strip to roll back into the preferred shape. Tabs 19 which have been formed on what is now the inside edge will engage the holes 17 formed in the strip and prevent collapse to the biased shape. Since a plurality of holes 17 are formed in the strip 21, the device may be expanded to different sizes, depending upon the particular vessel in which it is placed. Under some circumstances, the device is capable of assuming a stent shape with more than one diameter.

Figure 9:
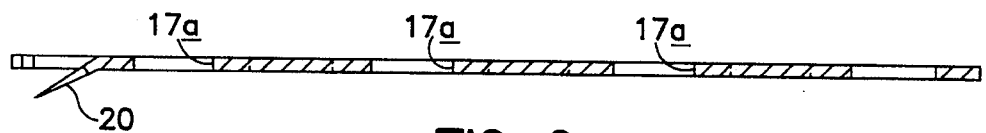
FIG. 9 is a sectional view taken on line 9,9 of FIG. 8.
Figure 10:
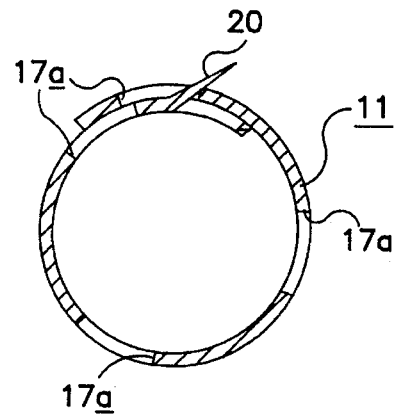
FIG. 10 is a sectional view similar to FIG. 4 but showing the endoprosthesis formed from the blank of FIG. 8.
Figure 11:
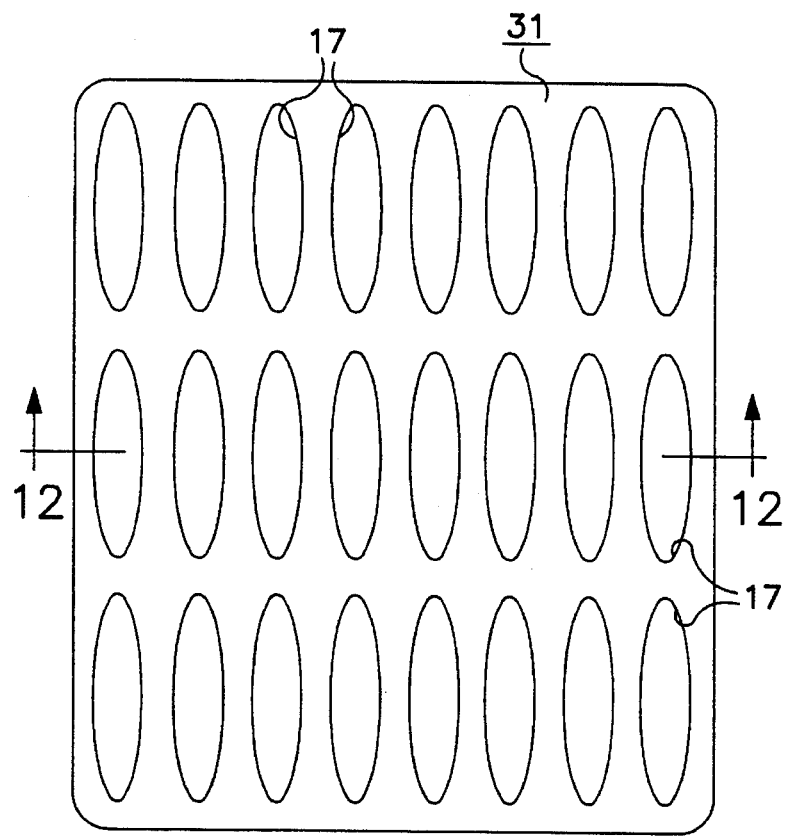
FIG. 11 is a plan view development of a third embodiment for an endoprosthesis blank.
Figure 12:
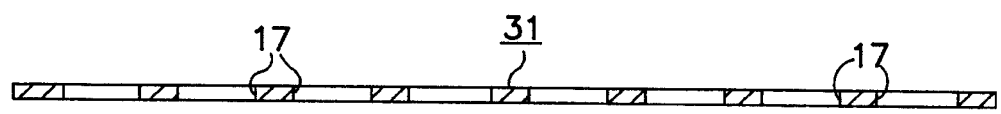
FIG. 12 is a sectional view taken along line 12,12 of FIG. 11.

A slightly different stent layout is shown in FIGS. 8–10, in that tabs 19 are replaced with pointed tabs 20. Again the coiled stent 11 is heated or otherwise biased to move to a collapsed or tightly coiled condition. Pointed tabs 20 engage holes 17 and prevent such recoiling. In addition, pointed tabs 20 engage the side walls of the blood vessel or other part of the anatomy where the stent has been deployed.

Figure 13:
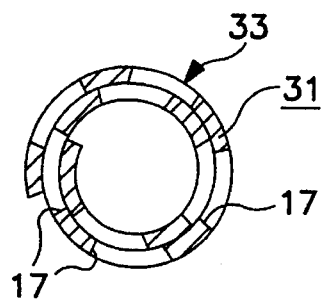
FIG. 13 is a sectional view similar to FIG. 4 but showing the endoprosthesis formed from the blank of FIG. 11.
Figure 14:
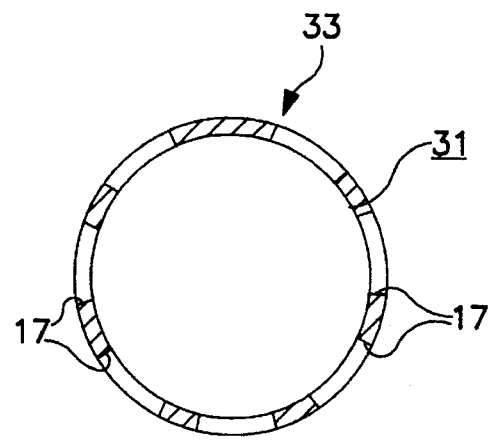
FIG. 14 is a view of the endoprosthesis of FIG. 13 after insertion and expansion in its position of intended use.

Turning now to FIGS. 11–14, an alternative embodiment is shown in which a strip 31 is formed into the desired size and shape, with holes 17 being provided for flexibility and for engagement with the tissue after implantation in some instances. No tabs are needed for this embodiment since this stent will have an outward biasing tendency. The stent assumes the shape shown in FIG. 14 after heating or otherwise forming the rolled stent into a usable configuration. When implantation is desired, the stent 33 is constricted to a smaller diameter as shown in FIG. 13, so that the bias of the design is to expand the stent. An introducter sheath of the type already in use should be used to position the stent in the vessel of choice. It may be only necessary to pull the sheath back to expose the stent.

In all of the devices of this invention, it is intended that a polymer form the exterior surface of the stent, either as a coating or as the stent itself. The drawings should be interpreted to understand that a polymer does form the exterior surface, whether or not a substrate such as a metal stent is used. The polymer should have a microporous structure with a predetermined pore size. Also included in the polymer is a bioactive substance having a charge distribution, concentration and molecular weight selected which achieves an equilibrium in relation to the pore size of the polymeric carrier with said surrounding body tissues or fluids.

Among these polymers are polymers having a microporous structure, such as silicone, polyurethane, polyvinyl alcohol, polyethylene, polyesters, hydrogels, tetrafluroethylene and polytetrafluoroethylene, fluorosilicone, hyaluronte and combinations, copolymers and blended mixtures thereof. One preferred resorbable polymer is biodegradable polylactic acid, and another is polyglycolic acid. These materials are suitable for being formed into a stent that possesses acceptable tensile strength characteristics.

If the stent is formed from a polymer, these same polymeric materials may be employed, although some may need to be structurally reinforced. Also useful as a polymeric stent is polymethylmethacrylate, which is an example of the generic class of polymers having good structural properties. In any event, the bioactive substance is incorporated into the polymer prior to insertion of the stent into the vessel.

Radio opaque substances such as, for example, fluorescein, may also be incorporated into the stent so as to assist in the deployment and subsequent evaluative follow-up of the surgery. A primary purpose of the bioactive substance is to inhibit vessel wall restenosis following vascular balloon angioplasty. In addition, stents of the present invention may be used to improve the diameter of the urethra or fallopian tubes, ureter, bile duct, trachea, esophagus, or other body vessel.

Preferred bioactive substances are heparin, hirudin, prostacyclenes and analogs thereof, antithrombogenic agents, steroids, ibuprofen, antimicrobials, antibiotics, tissue plasma activators, rifamicin, monoclonal antibodies, snake venom protein by-products, antifibrosis agents, cyclosporine, hyaluronte and mixtures of these bioactive substances for simultaneous multiple treatments. Of course, virtually any bioactive substance of need to the patient is a possible agent for treating the patient, depending upon the needs of the treatment.

The preparation of the stents of this invention is as follows. When a metallic stent is contemplated, and any of these stent designs may benefit from the concepts of this invention, a medical grade of polymer is selected. Preferred is a silicone elastomer. A quantity of silicone elastomer is mixed in a 3 to 1 ration with ethyl ether to form a solution suitable for coating a metallic stent. A quantity of bioactive substance required to achieve the desired therapeutic effect is admixed with the polymer and ethyl ether solution. After thorough blending, the now bioactivated polymer solution is ready to be used to coat the stent.

The cleaned metallic stent is coated by the bioactivated polymer using a variety of methods. One method is to completely submerge or dip the stent into a quantity of polymer so that the metallic stent is fully covered. After coating and removing from the dip, the polymer is cured or vulcanized at the desired temperature, depending upon the polymer. Alternatively, the polymer may be sprayed on to the polymer and then cured. Yet another method includes pouring a coating over the stent while the stent is being rotated. Plasma coating is also effective.

A variety of stent designs may be employed within the scope of the present invention as defined above. In one embodiment, the stent may take the form of a metallic wire stent. Alternatively the stent may be a metallic tube with alternating slots which form a wire-like mesh when expanded. The stent may be self-expanding or balloon expanded. With this stent a polymer embedded with a bioactive substance is used to cover the wire, leaving the space between the wire or mesh uncovered. Alternatively the polymer embedded with a bioactive substance may be used to cover the wire or mesh and fill in the spaces between the wires, thereby maximizing the polymer in contact with surrounding tissues. In both cases tissue ingrowth is permitted to encourage and facilitate rapid endothelialization, either with the spaces between the wires or in holes formed in the outer surface of the polymer as drugs are released to permit tissue ingrowth. Yet another embodiment would be to coat the outer surface of a fabric or other sheath material which is then used in combination with a metallic stent frame.

In addition, the stents described with respect to FIGS. 1–14 may be modified so that a flat sheet with multiple holes, such as stent 11 of FIGS. 1–4, with holes 17 but without tab 19. In this embodiment the spring-like properties of sheet 21 are sufficient to cause stent 11 to unroll to the desired size. In this embodiment, the polymer embedded with a bioactive substance is used to cover the flat portion 21 of stent 11 without occluding holes 17. Alternatively, holes 17 could also be covered by the polymer embedded with a bioactive substance as previously described with respect to a mesh stent and release of drugs from the outer surface of the polymer embedded with a bioactive substance will leave additional holes to permit and encourage tissue ingrowth.

In yet another embodiment, the flat sheet or mesh configuration may be composed entirely of polymer that is formed into the desired stent configuration directly without an accompanying substructure. The stent thus formed may be comprised of a polymer that is permanent, to give a long term structural support as the drugs are eluted, or the polymer may be biodegradable so that in time, as the treatment succeeds and tissue heals and rebuilds itself, the polymer will be absorbed by the body. Of course, long term treatment by the drugs within the polymer takes place in either case.

Finally, an additional embodiment is contemplated in which the polymer embedded with a bioactive substance is cured in situ at the diseased site so as to structurally support the vessel while treating the tissues via polymeric release. In this method, the non-cured polymer is injected into the vessel site via a catheter so as to 'coat' the surrounding vessel walls. The polymer is cured within the vessel to form a tubular layer or lining in direct contact with the surrounding tissues. As the drug is released, holes are again formed to permit ingrowth as has been described herein, particularly where the polymer is non-resorbable. When resorbable polymers are used to form the in-situ cured stent, tissue quickly displaces the polymer as it biodegrades, this permitting endothelialization.

While particular embodiments of the present invention have been illustrated and described, it is not intended to limit the invention, except as defined by the following claims.

I claim:

1. A minimally invasive bioactivated endoprosthesis device for vessel repair in contact with surrounding body tissues, comprising:

a stent formed from a solid non-biodegradable material presenting a substantial surface to said tissues for use with a blood vessel or other body conduit to form an internally unrestricted stent having a diameter of a selected size for said blood vessel or other body conduit; said stent including a plurality of holes sufficiently large to permit rapid endothelialization; and a polymer forming at least the exterior surface of said stent for direct polymer to tissue contact with said tissue, said polymer having a porous structure with a predetermined pore size and further including a bioactive substance within said pores for elution from said pores, said pore size being selected in response to the concentration and molecular weight of said substance to achieve equilibrium between said polymer and said tissue to provide a controlled and prolonged release of said bioactive substance to said surrounding body tissue in an amount sufficient to substantially prevent hyperplasia or therapeutically treat said tissue, said stent having sufficient amount of said substantial surface to support a quantity of said polymer capable of prolonged release of said amount.

2. A method of making a minimally invasive bioactivated endoprosthesis device for vessel repair in contact with surrounding body tissues, comprising the steps of:

forming a stent from a non-biodegradable material sized to present a substantial surface to said tissues for use with a blood vessel or other body conduit and having a diameter of a selected size for said blood vessel or other body conduit; said material including a plurality of holes sufficiently large to permit rapid endothelialization; and forming a polymer on at least the exterior surface of said stent for direct polymer to tissue contact with said tissues, said polymer having a porous structure with a predetermined pore size and further including a bioactive substance within said pores for elution from said pores, said pore size being selected in response to the concentration and molecular weight of said substance to achieve equilibrium between said polymer and said tissues to provide a controlled and prolonged release of said bioactive substance to said surrounding body tissues in an amount sufficient to substantially prevent hyperplasia or therapeutically treat said tissues, said stent having a sufficient amount of said substantial surface to support a quantity of said polymer capable of prolonged release of said amount.

3. The device of claim 1, wherein said stent comprises a substructure selected from the group consisting of flat sheets, flat sheets having holes therein, meshes and stent flames having a sheath thereon; said structure being coated with said polymer embedded with a bioactive substance.

4. The device of claim 1, wherein said stent is formed in-situ from said polymer embedded with a bioactive substance wherein the polymer is cured after placement in contact with surrounding tissues.

5. The device of claim 1, wherein said stent comprises a metallic substructure having said polymer as a coating.

6. The device of claim 1 wherein said polymer is selected from the group of silicone, polyurethane, polyvinyl alcohol, polyethylene, biodegradable polylactic acid polymers, polyglycolic acid polymers, polyesters, hydrogels, polytetrafluroethylene, fluorosilicone, hyaluronte and combinations, copolymers and blended mixtures thereof.

7. The device of claim 1, wherein said bioactive substance is selected from the group consisting of heparin, hirudin, prostacyclenes or analogs thereof, antithrombogenic agents, steroids, ibuprofen, antimicrobials, antibiotics, tissue plasma activators, rifamicin, monoclonal antibodies, snake venom protein by-products, antifibrosis agents, hyaluronte, cyclosporine and mixtures of these bioactive substances for simultaneous multiple treatments.

8. The device of claim 1 wherein said stent is formed solely from said polymer having sufficient structural integrity to be formed into a stent.

9. The method of claim 2, wherein said stent is formed from a substructure selected from the group consisting of flat sheets, flat sheets having holes therein, meshes and stent frames having a sheath thereon; said structure being coated with said polymer embedded with a bioactive substance.

10. The method of claim 2, wherein said stent is formed in-situ from a polymer embedded with a bioactive substance wherein the polymer is cured after placement in contact with surrounding tissues.

11. The method of claim 2, wherein said stent is selected from the group consisting of self-expanding and mechanically expandable stents.

* * * * *

REEXAMINATION CERTIFICATE (3992nd)

United States Patent
Dayton

[11] B1 5,578,075
[45] Certificate Issued   *Feb. 8, 2000

[54] MINIMALLY INVASIVE BIOACTIVATED ENDOPROSTHESIS FOR VESSEL REPAIR

[75] Inventor: Michael P. Dayton, Tampa, Fla.

[73] Assignee: Daynke Research, Inc., Tampa, Fla.

Reexamination Request:
No. 90/005,278, Mar. 1, 1999

Reexamination Certificate for:
Patent No.:  5,578,075
Issued:      Nov. 29, 1996
Appl. No.:   08/457,850
Filed:       Jun. 1, 1995

[ * ] Notice: This patent is subject to a terminal disclaimer.

Related U.S. Application Data

[63] Continuation-in-part of application No. 08/204,947, Mar. 2, 1994, Pat. No. 5,449,382, which is a continuation of application No. 07/971,217, Nov. 4, 1992, abandoned.

[51] Int. Cl.$^7$ ........................................... A61F 2/06
[52] U.S. Cl. ............................ 623/1; 6223/12; 6223/901; 604/104; 604/107

[56] References Cited

U.S. PATENT DOCUMENTS

| | | | |
|---|---|---|---|
| 4,740,207 | 4/1988 | Kreamer | 623/12 |
| 4,923,464 | 5/1990 | DiPisa . | |
| 4,969,890 | 11/1990 | Sugita . | |
| 4,994,071 | 2/1991 | MacGregor . | |
| 5,019,090 | 5/1991 | Pinchuk | 623/1 |
| 5,102,417 | 4/1992 | Palmaz . | |
| 5,123,917 | 6/1992 | Lee | 623/1 |
| 5,222,971 | 6/1993 | Willard . | |
| 5,234,456 | 8/1993 | Silvestrini | 623/1 |
| 5,282,823 | 2/1994 | Schwartz . | |
| 5,304,121 | 4/1994 | Sahatjian . | |
| 5,342,348 | 8/1994 | Kaplan | 623/13 |
| 5,344,426 | 9/1994 | Lau et al. | 623/1 |
| 5,423,885 | 6/1995 | Williams . | |
| 5,441,515 | 8/1995 | Khosravi et al. | 606/194 |
| 5,443,458 | 8/1995 | Eury . | |
| 5,443,496 | 8/1995 | Schwartz . | |
| 5,449,382 | 9/1995 | Dayton | 623/12 |
| 5,464,450 | 11/1995 | Buscemi et al. | 623/12 |
| 5,512,055 | 4/1996 | Domb . | |
| 5,545,208 | 8/1996 | Wolff . | |
| 5,591,227 | 1/1997 | Dinh . | |
| 5,649,977 | 7/1997 | Campbell | 623/1 |
| 5,700,286 | 12/1997 | Tartaglia et al. | 623/1 |

FOREIGN PATENT DOCUMENTS

| | | |
|---|---|---|
| 0470246B1 | 6/1995 | European Pat. Off. . |
| WO90/13332 | 11/1990 | WIPO . |
| WO91/12779 | 9/1991 | WIPO . |

*Primary Examiner*—Paul Prebilic

[57] ABSTRACT

A minimally invasive bioactivated endoprosthesis device for vessel repair. The device comprises a stent which is formed from metal or polymers into a predetermined shape which may include a plurality of holes patterend with a desired size, shape and number. The stent is then coated with a polymer or is formed from a polymer which contains a bioactive substance which achieves an equilibrium with the surrounding body tissues or fluids, with the equilibrium being controlled by charge distribution, concentration and molecular weight of the bioactive substance in relation to the pore size of the polymeric carrier for controlled prolonged release of said bioactive substance. The bioactive substance may be selected from the group of heparin, hirudin, prostacyclenes and analogs thereof, antithrombogenic agents, steroids, ibuprofen, antimicrobials, antibiotics, tissue plasma activators, rifamicin, monoclonal, antibodies, snake venom protein by-products, antifibrosis agents, hyaluronte, cyclosporine and mixtures of these bioactive substances for simultaneous multiple treatments. The stent itself may take several distinct configurations. Preferred is a stent which comprises a substructure selected from flat sheets, flat sheets having holes therein, meshes and stent frames having a sheath thereon, and the substructure is coated with a polymer embedded with a bioactive substance. The stent may be either self-expandable or mechanically expandable, such as by a balloon or other device.

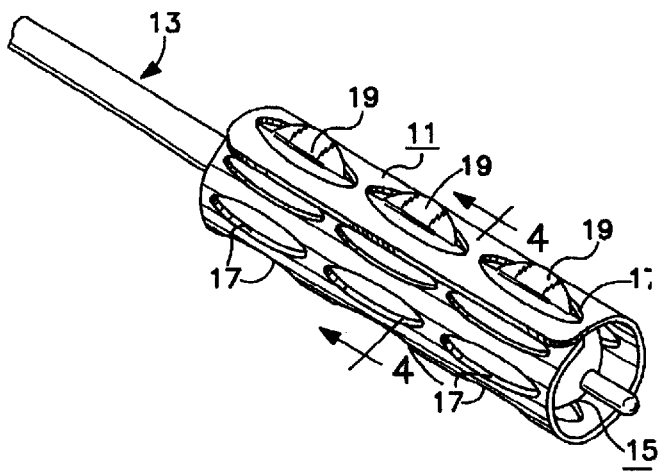

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1, 2, and 4–11 is confirmed.

Claim 3 is determined to patentable as amended.

3. The device of claim 1, wherein said stent comprises a substructure selected from the group consisting of flat sheets, flat sheets having holes therein, meshes and stent [flames] *frames* having a sheath thereon; said structue being coated with said polymer embedded with a bioactive substance.

* * * * *